(12) United States Patent
McElroy

(10) Patent No.: US 6,323,236 B2
(45) Date of Patent: *Nov. 27, 2001

(54) USE OF SULFAMATE DERIVATIVES FOR TREATING IMPULSE CONTROL DISORDERS

(75) Inventor: Susan McElroy, Cincinnati, OH (US)

(73) Assignee: University of Cincinnati, Cincinnati, OH (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/506,991

(22) Filed: Feb. 18, 2000

Related U.S. Application Data

(60) Provisional application No. 60/121,339, filed on Feb. 24, 1999.

(51) Int. Cl.[7] .................... A61K 31/385; A61K 31/35; A61K 31/335
(52) U.S. Cl. ................ 514/439; 514/455; 514/459; 514/463
(58) Field of Search .................. 514/455, 439, 514/459, 463

(56) References Cited

U.S. PATENT DOCUMENTS

| | | |
|---|---|---|
| 4,513,006 | 4/1985 | Maryanoff et al. . |
| 6,071,537 | 6/2000 | Shank . |

FOREIGN PATENT DOCUMENTS

| | | |
|---|---|---|
| 0568306A | 11/1993 | (WO) . |
| WO9800123A | 1/1998 | (WO) . |
| WO9800130A | 1/1998 | (WO) . |
| WO0007583A | 2/2000 | (WO) . |

(List continued on next page.)

OTHER PUBLICATIONS

McElroy, S. L. et al, "Are Impulse—Control Disorders Related To Bipolar Disorder?", Comprehensive Psychiatry, (1996) 37/4 (229–240).

Potter, D. et al., "Sustained Weight Loss Associated with 12–month Topiramate Therapy", Epilepsia, U.S., Raven Press Ltd., New York, vol. 38, No. Suppl. 08, 1997, p. 97.

K.T. Brady et al., "The Relationship Between Subtance Use Disorders, Impulse Control Disorders, and Pathological Aggression", American Journal of Addictions, vol. 7, No. 3, 1998, pp. 221–230.

Kuziecky R. et al., "Topiramate Increase Cerebral Gaba in Healthy Humans", Neurology, Lippincott Williams, & Wilkins, Philadelphia, U.S., No. 51, Aug. 1998 (1998–08), pp. 627–629.

Marcotte D, "Use of Topiramate, A New Anti–Epileptic As a Mood Stabilizer", Journal of Affective Disorders, NL, Elsevier Biochemical Press, Amsterdam, vol. 50. No. 2/03, Sep. 1998 (1998–09), pp. 245–251.

Dewey S.L. et al., "A Pharmacologic Strategy For The Treatment of Nicotine Addiction", Synapse, G.B., Wiley and Sons, Chichester, vol. 31, No. 1, Jan. 1999 (1999–01), pp. 76–86.

R.L. Spitzer, S. Yanovski, T. Wadden, et al., Binge Eating Disorder: Its Further Validation in a Multisite Study, *International Journal of Eating Disorders*, vol. 13, pp. 137–153, 1993.

M.D. Privitera, Topiramate: A New Antiepileptic Drug, *Annals of Pharmacotherapy*, vol. 31, pp. 1164–1173, 1997.

B.G. Stanley, L.H. Ha, L.C. Spears, et al., Lateral Hypothalamic Injections of Glutamate, Kainic Acid, D,L–alpha–amino–3–hydroxy–5–methyl–isoxazole proprionic acid or N–methyl–D–aspartic acid Rapidly Elicit Intense Transient Eating in Rats, *Brain Research*, vol. 613, pp. 88–95, 1993.

B. G. Stanley, V.L. Willett, III, H.W. Donias, et al., the Lateral Hypothalamus: a Primary Site Mediating Excitatory Amino Acid–elicited Eating, *Brain Research*, vol. 630, pp. 1–49, 1993.

R.S. Green, J.H. Rau, Treatment of Compulsive Eating Disturbances with Anticonvulsant Medication, *American Journal of Psyschiatry*, vol. 131, pp. 428–432, 1974.

J. L. Hudson, S.L. McElroy N.C. Raymond, et al., Fluvoxamine in the Treatment of Binge Eating Disorder: a Multi Center Placebo–Controlled Double–Blind Trial, *American Journal of Psychiatry*, vol. 155, pp. 1756–1762, 1998.

(List continued on next page.)

*Primary Examiner*—William R. A. Jarvis
(74) *Attorney, Agent, or Firm*—Frost Brown Todd LLC

(57) ABSTRACT

Impulse Control Disorders (ICD's) are characterized by harmful behaviors performed in response to irresistible impulses. The essential feature of an ICD is the failure to resist an impulse, drive, or temptation and to perform an act that is harmful to the person or to others. The present invention comprises methods for the treatment or prevention of ICD's using a class of sulfamates of the following formula:

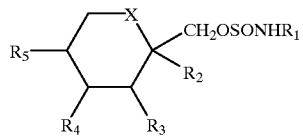

(I)

wherein X is $CH_2$ or oxygen, and $R_1$, $R_2$, $R_3$, $R_4$ and $R_5$ are as herein defined. Further, pharmaceutical compositions containing a compound of formula (I) as well as methods for their use and intermediates form part of the present invention are also disclosed.

16 Claims, No Drawings

FOREIGN PATENT DOCUMENTS

| | | |
|---|---|---|
| WO0023059A | 4/2000 | (WO) . |
| WO0044374A | 8/2000 | (WO) . |
| WO061140A | 10/2000 | (WO) . |
| WO0066108A | 11/2000 | (WO) . |
| WO0076943 | 12/2000 | (WO) . |

OTHER PUBLICATIONS

L.L. Alshuler, R.M. Post, G.S. Leverich, et al., Antidepressant–induced Mania and Cycle Acceleration: a Controversy Revisited, American Journal of Psychiatry, vol. 152, pp. 1130–1138, 1996.

F. Benazzi, Antidepressant–Associated Hypomania in Outpatient Depression: a 203–Case Study in Private Practice, *Journal of Affectic Disorders*, vol. 46, pp. 73–77, 1997.

S. Kruger, G. Shugar, R.G. Cooke, Comorbidity of Binge Eating Disorder and the Partial Binge Eating Syndrome with Bipolar Syndrome, *International Journal of Eating Disorders*, vol. 19, pp. 45–52, 1996.

A.J. Stunkard, Eating Pattern and Obesity, *Psychiatric Quarterly*, vol. 33, pp. 284–292, 1959.

American Psychiatric Association, Diagnostic and Statistical Manual for Mental Disorders, *American Psychiatric Association*, 4th Ed. Washington, DC, 1994, Table of Contents only.

M. Mitchell DeZwaan, J.E. Mitchell, N.C. Raymond, et al., Binge Eating Disorder: Clinical Features and Treatment of a New Diagnosis, *Harvard Review of Psychiatry*, Vol. 1, pp. 310–325, 1994.

R.L. Spitzer, M. Devlin, B.T. Walsh, et al., Binge Eating Disorder: a multisite field trial of the diagnostic criteria, *International Journal of Eating Disorders*, vol. 11, pp. 191–203, 1992.

J.R. Calabrese, M.D. Shelton, III, P.E. Keck, Jr., et al., Topiramate in Severe Treatment–Refractory Mania, *New Research Program and Abstracts of the 151$^{st}$ Annual Meeting of the American Psychiatry Association; Tononto, Canada Abstract NR 202:121–122, Jun. 2, 1998.

JJ.I. Hudson, H.G. Pope, The role of Anticonvulsants in the Treatment of Bulimia, S.L. McElroy, H.G. Pope, eds. "Use of Anticonvulsants in Psychiatry: Recent Advances," Clifton, NJ, *Oxford Health Care*, pp. 141–145, 1988.

USE OF SULFAMATE DERIVATIVES FOR TREATING IMPULSE CONTROL DISORDERS

This application claims priority to U.S. Provisional Patent Application Ser. No. 60/121,339, filed Feb. 24, 1999.

TECHNICAL FIELD

The present invention generally relates to the use of drugs for the treatment of mental disorders. More specifically, the invention describes methods for the treatment and prevention of Impulse Control Disorders (ICD's) by administering sulfamate derivatives.

BACKGROUND OF THE INVENTION

Sulfamate derivatives having useful pharmaceutical activity in the areas of epilepsy, glaucoma, peptic ulcers and male infertility are disclosed in U.S. Pat. Nos. 4,075,351, 4,513,006, 4,591,601, 4,792,569, and 5,760,007. One of these compounds 2,3:4,5-bis-O-(1-methylethylidene)-beta-D-fructopyranose sulfamate known as topiramate has been demonstrated in clinical trials of human epilepsy to be effective as adjunctive therapy or as monotherapy in treating simple and complex partial seizures and secondarily generalized seizures and is currently marketed for the treatment of simple and complex partial seizure epilepsy with or without secondary generalized seizures.

Binge eating disorder (BED) is characterized by discrete periods of binge eating during which large amounts of food are consumed in a discrete period of time and a sense of control over eating is absent. Persons with bulimia nervosa have been reported to have electroencephalographic abnormalities and to display reduced binge eating in response to the anti-epileptic drug phenytoin. Also, in controlled trials in patients with epilepsy, topiramate was associated with suppression of appetite and weight loss unreleated to binge eating.

Binge eating disorder is a subset of a larger classification of mental disorders broadly defined as Impulse Control Disorders (ICDs) characterized by harmful behaviors performed in response to irresistible impulses. It has been suggested that ICDs may be related to obsessive-compulsive disorder or similarly, maybe forms of obsessive-complusive disorders. It has also been hypothesized that ICDs may be related to mood disorder or may be forms of affective spectrum disorder, a hypothesized family of disorders sharing at least one common physiologic abnormality with major depression. In the Diagnostic and Statistical Manual of Mental Disorders (DSM-IV), the essential feature of an ICD is the failure to resist an impulse, drive, or temptation to perform an act that is harmful to the person or to others. For most ICDs, the individual feels an increasing sense of tension or arousal before committing the act, and then experiences pleasure, gratification, or release at the time of committing the act. After the act is performed, there may or may not be regret or guilt. ICDs are listed in a residual category, the ICDs Not Elsewhere Classified, which includes intermittent explosive disorder (IED), kleptomania, pathological gambling, pyromania, trichotillomania, and ICD not otherwise specified (NOS). Examples of ICDs NOS are compulsive buying or shopping, repetitive self-mutilation, nonparaphilic sexual addictions, severe nail biting, compulsive skin picking, personality disorders with impulsive features, attention deficit/hyperactivity disorder, eating disorders characterized by binge eating, and substance use disorders.

SUMMARY OF THE INVENTION

It is an object of the present invention to describe the use of sulfamate derivatives for the treatment of Impulse Control Disorders.

The present invention comprises methods for the treatment or prevention of Impulse Control Disorders using the compounds of formula (I), pharmaceutical compositions containing one or more of the compounds of formula (I), or pharmaceutical compositions containing one or more of the compounds of formula (I) in addition to a safe and effective amount of one or more additional agents to treat related symptoms and conditions.

DETAILED DESCRIPTION OF THE INVENTION

The sulfamates of use in the present invention are of the following formula (I):

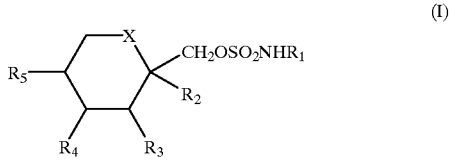

(I)

wherein

X is $CH_2$ or oxygen;

$R_1$ is hydrogen or alkyl; and $R_2$, $R_3$, $R_4$ and $R_5$ are independently hydrogen or lower alkyl and, when X is $CH_2$, $R_4$ and $R_5$ may be alkene groups joined to form a benzene ring and, when X is oxygen, $R_2$ and $R_3$ and/or $R_4$ and $R_5$ together may be a methylenedioxy group of the following formula (II):

(II)

wherein $R_6$ and $R_7$ are the same or different and are hydrogen, lower alkyl or are alkyl and are joined to form a cyclopentyl or cyclohexyl ring. $R_1$ in particular is hydrogen or alkyl of about 1 to 4 carbons, such as methyl, ethyl and iso-propyl. Alkyl throughout this specification includes straight and branched chain alkyl. Alkyl groups for $R_2$, $R_3$, $R_4$, $R_5$, $R_6$ and $R_7$ are of about 1 to 3 carbons and include methyl, ethyl, iso-propyl and n-propyl. When X is $CH_2$, $R_4$ and $R_5$ may combine to form a benzene ring fused to the 6-membered X-containing ring, i.e., $R_4$ and $R_5$ are defined by the alkatrienyl group $=C-CH=CH-CH=$.

A particular group of compounds of formula (I) is that wherein X is oxygen and both $R_2$ and $R_3$ and $R_4$ and $R_5$ together are methylenedioxy groups of the formula (II), wherein $R_6$ and $R_7$ are both hydrogen, both alkyl or combine to form a spiro cyclopentyl or cyclohexyl ring, in particular where $R_6$ and $R_7$ are both alkyl such as methyl. A second group of compounds is that wherein X is $CH_2$ and $R_4$ and $R_5$ are joined to form a benzene ring. A third group of compounds of formula (I) is that wherein both $R_2$ and $R_3$ are hydrogen.

The compounds of formula I: may be made by the processes disclosed in U.S. Pat. Nos. 4,075,351, 4,513,006, 4,591,601, 4,792,569, 5,242,942, 5,387,700, which are incorporated in their entirety herein by reference.

The compounds of formula I include the various individual isomers as well as the racemates thereof. For treating ICDs, a compound of formula (I) may be employed at a daily dosage in the range of about 15 to 1400 mg administered orally, for an average adult human.

To prepare the pharmaceutical compositions of this invention, one or more sulfamate compounds of formula (I) are intimately admixed with a pharmaceutical carrier according to conventional pharmaceutical compounding techniques, which carrier may take a wide variety of forms depending on the form of preparation desired for administration, e.g., oral, by suppository, or parenteral. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. Suppositories may be prepared, in which case cocoa butter could be used as the carrier. For parenterals, the carrier will usually comprise sterile water, though other ingredients, for example, for purposes such as aiding solubility or for preservation, may be included. Injectable suspensions may also be prepared in which case appropriate liquid carriers, suspending agents and the like may be employed. Topiramate is currently available for oral administration in round tablets containing 25 mg, 100 mg or 200 mg of active agent. The tablets contain the following inactive ingredients: lactose hydrous, pregelatinized starch, microcrystalline cellulose, sodium starch glycolate, magnesium stearate, purified water, carnauba wax, hydroxypropyl methylcellulose, titanium dioxide, polyethylene glycol, synthetic iron oxide, and polysorbate 80.

The pharmaceutical compositions herein will contain, per dosage unit, e.g., tablet, capsule, powder injection, teaspoonful, suppository and the like from about 5 to about 1000 mg of the active ingredient.

The activity of the compounds of formula I in treating ICD's was first evidenced in clinical studies conducted to evaluate the efficacy of topiramate in treating mood disorders. Several patients who coincidentally had binge eating disorder reported that there was a marked reduction in their binging and a concurrent loss in weight.

Examples of specific compounds of formula (I) are:

2,3:4,5-bis-O-(1-methylethylidene)-beta-D-fructopyranose sulfamate
2,3-O-(1-methylethylidene)-4,5-O-sulfonyl-beta-D-fructopyranose sulfamate;
2,3-O-(1-methylethylidene)-4,5-O-sulfonyl-beta-L-fructopyranose sulfamate;
2,3-O-(1-methylethylidene)-4,5-O-sulfonyl-beta-D-fructopyranose methylsulfamate;
2,3-O-(1-methylethylidene)-4,5-O-sulfonyl-beta-D-fructopyranose butylsulfamate;
2,3-O-(1-methylethylidene)-4,5-O-sulfonyl-beta-D-fructopyranose ethylsulfamate;
2,3-O-(1-methylethylidene)-4,5-O-sulfonyl-beta-D-fructopyranose octylsulfamate;
2,3-O-(1-methylethylidene)-4,5-O-sulfonyl-beta-D-fructopyranose 2-propenylsulfamate;
2,3-O-(1-methylethylidene)-4,5-O-sulfonyl-beta-D-fructopyranose phenylmethylsulfamate;
2,3-O-(1-methylethylidene)-4,5-O-sulfonyl-beta-D-fructopyranose cyclopropylsulfamate;
2,3-O-(1-methylethylidene)-4,5-O-sulfonyl-beta-D-fructopyranose cyclobutylsulfamate;
2,3-O-(1-methylethylidene)-4,5-O-sulfonyl-beta-D-fructopyranose (2,2,2-trifluoroethyl)sulfamate;
2,3-O-(1-methylethylidene)-4,5-O-sulfonyl-beta-D-fructopyranose dimethylsulfamate;
2,3-O-(1-methylethylidene)-4,5-O-sulfonyl-beta-D-fructopyranose diethylsulfamate;
2,3-O-(1-methylethylidene)-4,5-O-sulfonyl-beta-D-fructopyranose azidosulfamate;
(S)-2,3-O-(1-methylethylidene)-4,5-O-sulfinyl-beta-D-fructopyranose sulfamate;
(R)-2,3-O-(1-methylethylidene)-4,5-O-sulfinyl-beta-D-fructopyranose sulfamate;
2,3-O-(1-ethylpropylidene)-4,5-O-sulfonyl-beta-D-fructopyranose sulfamate;
2,3-O-(1-methylethylidene)-4,5-O-[N-(4-methylbenzenesulfonyl)imidosulfinyl]-beta-D-fructopyranose sulfamate;
2,3-O-(1-methylethylidene)-4,5-O-[N-(4-methylbenzenesulfonyl)imidosulfonyl]-beta-D-fructopyranose sulfamate;
2,3-O-(cyclohexylidene)-4,5-O-sulfonyl-beta-D-fructopyranose sulfamate;
(S)-4,5-O-[N-(1,1-dimethylethoxycarbonyl)imidosulfinyl]-2,3-O-(1-methylethylidene)-beta-D-fructopyranose sulfamate;

and the pharmaceutically acceptable salts thereof

Included within the scope of this invention are the various individual anomers, diastereomers and enantiomers as well as mixtures thereof. Such compounds are included within the definition of formula (I). In addition, the compounds of this invention also include any pharmaceutically acceptable salts, for example: alkali metal salts, such as sodium and potassium; ammonium salts; monoalkylammonium salts; dialkylammonium salts; trialkylammonium salts; tetraalkylammonium salts; and tromethamine salts. Hydrates and other solvates of the compound of the formula (I) are included within the scope of this invention.

Pharmaceutically acceptable salts of the compounds of formula (I) can be prepared by reacting the sulfamate of formula (I) with the appropriate base and recovering the salt.

The sulfamate derivatives may be used in conjunction with one or more other drug compound and used according to the methods of the present invention so long as the pharmaceutical agent has a use that is also effective in treating ICD's and/or concurrent illnesses. Pharmaceutical agents include the following categories and specific examples. It is not intended that the category be limited by the specific examples. Those of ordinary skill in the art will be able to identify readily those pharmaceutical agents that have utility with the present invention. Those of ordinary skill in the art will recognize also numerous other compounds that fall within the categories and that are useful according to the invention.

Adrenergic: Adrenalone; Amidephrine Mesylate; Apraclonidine Hydrochloride; Brimonidine Tartrate; Dapiprazole Hydrochloride; Deterenol Hydrochloride; Dipivefrin;

Dopamine Hydrochloride; Ephedrine Sulfate; Epinephrine; Epinephrine Bitartrate; Epinephryl Borate; Esproquin Hydrochloride; Etafedrine Hydrochloride; Hydroxyamphetamine Hydrobromide; Levonordefrin; Mephentermine Sulfate; Metaraminol Bitartrate; Metizoline Hydrochloride; Naphazoline Hydrochloride; Norepinephrine Bitartrate; Oxidopamine; Oxymetazoline Hydrochloride; Phenylephrine Hydrochloride; Phenylpropanolamine Hydrochloride; Phenylpropanolamine Polistirex; Prenalterol Hydrochloride; Propylhexedrine; Pseudoephedrine Hydrochloride; Tetrahydrozoline Hydrochloride; Tramazoline Hydrochloride; Xylometazoline Hydrochloride.

Adrenocortical steroid: Ciprocinonide; Desoxycorticosterone Acetate; Desoxycorticosterone Pivalate; Dexamethasone Acetate; Fludrocortisone Acetate; Flumoxonide; Hydrocortisone Hemisuccinate; Methylprednisolone Hemisuccinate; Naflocort; Procinonide; Timobesone Acetate; Tipredane.

Adrenocortical suppressant: Aminoglutethimide; Trilostane.

Alcohol deterrent: Disulfiram.

Aldosterone antagonist: Canrenoate Potassium; Canrenone; Dicirenone; Mexrenoate Potassium; Prorenoate Potassium; Spironolactone.

Amino acid: Alanine; Aspartic Acid; Cysteine Hydrochloride; Cystine; Histidine; Isoleucine; Leucine; Lysine; Lysine Acetate; Lysine Hydrochloride; Methionine; Phenylalanine; Proline; Serine; Threonine; Tryptophan; Tyrosine; Valine.

Analeptic: Modafinil.

Analgesic: Acetaminophen; Alfentanil Hydrochloride; Aminobenzoate Potassium; Aminobenzoate Sodium; Anidoxime; Anileridine; Anileridine Hydrochloride; Anilopam Hydrochloride; Anirolac; Antipyrine; Aspirin; Benoxaprofen; Benzydamine Hydrochloride; Bicifadine Hydrochloride; Brifentanil Hydrochloride; Bromadoline Maleate; Bromfenac Sodium; Buprenorphine Hydrochloride; Butacetin; Butixirate; Butorphanol; Butorphanol Tartrate; Carbamazepine; Carbaspirin Calcium; Carbiphene Hydrochloride; Carfentanil Citrate; Ciprefadol Succinate; Ciramadol; Ciramadol Hydrochloride; Clonixeril; Clonixin; Codeine; Codeine Phosphate; Codeine Sulfate; Conorphone Hydrochloride; Cyclazocine; Dexoxadrol Hydrochloride; Dexpemedolac; Dezocine; Diflunisal; Dihydrocodeine Bitartrate; Dimefadane; Dipyrone; Doxpicomine Hydrochloride; Drinidene; Enadoline Hydrochloride; Epirizole; Ergotamine Tartrate; Ethoxazene Hydrochloride; Etofenamate; Eugenol; Fenoprofen; Fenoprofen Calcium; Fentanyl Citrate; Floctafenine; Flufenisal; Flunixin; Flunixin Meglumine; Flupirtine Maleate; Fluproquazone; Fluradoline Hydrochloride; Flurbiprofen; Hydromorphone Hydrochloride; Ibufenac; Indoprofen; Ketazocine; Ketorfanol; Ketorolac Tromethamine; Letimide Hydrochloride; Levomethadyl Acetate; Levomethadyl Acetate Hydrochloride; Levonantradol Hydrochloride; Levorphanol Tartrate; Lofemizole Hydrochloride; Lofentanil Oxalate; Lorcinadol; Lomoxicam; Magnesium Salicylate; Mefenamic Acid; Menabitan Hydrochloride; Meperidine Hydrochloride; Meptazinol Hydrochloride; Methadone Hydrochloride; Methadyl Acetate; Methopholine; Methotrimeprazine; Metkephamid Acetate; Mimbane Hydrochloride; Mirfentanil Hydrochloride; Molinazone; Morphine Sulfate; Moxazocine; Nabitan Hydrochloride; Nalbuphine Hydrochloride; Nalmexone Hydrochloride; Namoxyrate; Nantradol Hydrochloride; Naproxen; Naproxen Sodium; Naproxol; Nefopam Hydrochloride; Nexeridine Hydrochloride; Noracymethadol Hydrochloride; Ocfentanil Hydrochloride; Octazamide; Olvanil; Oxetorone Fumarate; Oxycodone; Oxycodone Hydrochloride; Oxycodone Terephthalate; Oxymorphone Hydrochloride; Pemedolac; Pentamorphone; Pentazocine; Pentazocine Hydrochloride; Pentazocine Lactate; Phenazopyridine Hydrochloride; Phenyramidol Hydrochloride; Picenadol Hydrochloride; Pinadoline; Pirfenidone; Piroxicam Olamine; Pravadoline Maleate; Prodilidine Hydrochloride; Profadol Hydrochloride; Propirarn Fumarate; Propoxyphene Hydrochloride; Propoxyphene Napsylate; Proxazole; Proxazole Citrate; Proxorphan Tartrate; Pyrroliphene Hydrochloride; Remifentanil Hydrochloride; Salcolex; Salethamide Maleate; Salicylamide; Salicylate Meglumine; Salsalate; Sodium Salicylate; Spiradoline Mesylate; Sufentanil; Sufentanil Citrate; Talmetacin; Talniflumate; Talosalate; Tazadolene Succinate; Tebufelone; Tetrydamine; Tifurac Sodium; Tilidine Hydrochloride; Tiopinac; Tonazocine Mesylate; Tramadol Hydrochloride; Trefentanil Hydrochloride; Trolamine; Veradoline Hydrochloride; Verilopam Hydrochloride; Volazocine; Xorphanol Mesylate; Xylazine Hydrochloride; Zenazocine Mesylate; Zomepirac Sodium; Zucapsaicin.

Anorectic compounds including dexfenfluramine.

Anorexic: Aminorex; Amphecloral; Chlorphentermine Hydrochloride; Clominorex; Clortennine Hydrochloride; Diethylpropion Hydrochloride; Fenfluramine Hydrochloride; Fenisorex; Fludorex; Fluminorex; Levamfetamine Succinate; Mazindol; Mefenorex Hydrochloride; Phenmetrazine Hydrochloride; Phentermine; Sibutramine Hydrochloride.

Anti-anxiety agent: Adatanserin Hydrochloride; Alpidem; Binospirone Mesylate; Bretazenil; Glemanserin; Ipsapirone Hydrochloride; Mirisetron Maleate; Ocinaplon; Ondansetron Hydrochloride; Panadiplon; Pancopride; Pazinaclone; Serazapine Hydrochloride; Tandospirone Citrate; Zalospirone Hydrochloride.

Antidepressant: Adatanserin Hydrochloride; Adinazolam; Adinazolam Mesylate; Alaproclate; Aletamine Hydrochloride; Amedalin Hydrochloride; Amitriptyline Hydrochloride; Amoxapine; Aptazapine Maleate; Azaloxan Fumarate; Azepindole; Azipramine Hydrochloride; Bipenarnol Hydrochloride; Bupropion Hydrochloride; Butacetin; Butriptyline Hydrochloride; Caroxazone; Cartazolate; Ciclazindol; Cidoxepin Hydrochloride; Cilobamine Mesylate; Clodazon Hydrochloride; Clomipramine Hydrochloride; Cotinine Fumarate; Cyclindole; Cypenamine Hydrochloride; Cyprolidol Hydrochloride; Cyproximide; Daledalin Tosylate; Dapoxetine Hydrochloride; Dazadrol Maleate; Dazepinil Hydrochloride; Desipramine Hydrochloride; Dexamisole; Deximafen; Dibenzepin Hydrochloride; Dioxadrol Hydrochloride; Dothiepin Hydrochloride; Doxepin Hydrochloride; Duloxetine Hydrochloride; Eclanamine Maleate; Encyprate; Etoperidone Hydrochloride; Fantridone Hydrochloride; Fehmetozole Hydrochloride; Fenmetramide; Fezolamine Fumarate; Fluotracen Hydrochloride; Fluoxetine; Fluoxetine Hydrochloride; Fluparoxan Hydrochloride; Gamfexine; Guanoxyfen Sulfate; Imafen Hydrochloride; Imiloxan Hydrochloride; Imipramine Hydrochloride; Indeloxazine Hydrochloride; Intriptyline Hydrochloride; Iprindole; Isocarboxazid; Ketipramine Fumarate; Lofepramine Hydrochloride; Lortalamine; Maprotiline; Maprotiline Hydrochloride; Melitracen Hydrochloride; Milacemide Hydrochloride; Minaprine Hydrochloride; Mirtazapine; Moclobemide; Modaline Sulfate; Napactadine Hydrochloride; Napamezole Hydrochloride; Nefazodone Hydrochloride; Nisoxetine; Nitrafudam Hydrochloride; Nomifensine Maleate; Nortriptyline Hydrochloride; Octriptyline Phosphate; Opipramol Hydrochloride; Oxaprotiline Hydrochloride; Oxypertine; Paroxetine; Phenelzine Sulfate; Pirandamine Hydrochloride; Pizotyline; Pridefine Hydrochloride; Prolintane Hydrochloride; Protriptyline Hydrochloride; Quipazine Maleate; Rolicyprine; Seproxetine Hydrochloride; Sertraline Hydrochloride; Sibutramine Hydrochloride; Sulpiride; Suritozole; Tametraline Hydrochloride; Tampramine Fumarate; Tandamine Hydrochloride; Thiazesim Hydrochloride; Thozalinone; Tomoxetine Hydrochloride; Trazodone Hydrochloride; Trebenzomine Hydrochloride; Trimipramine; Trimipramine Maleate; Venlafaxine Hydrochloride; Viloxazine Hydrochloride; Zimeldine Hydrochloride; Zometapine.

Antihypertensive: Aflyzosin Hydrochloride; Alipamide; Althiazide; Amiquinsin Hydrochloride; Amlodipine Besylate; Amlodipine Maleate; Anaritide Acetate; Atiprosin Maleate; Belfosdil; Bemitradine; Bendacalol Mesylate; Bendroflumethiazide; Benzthiazide; Betaxolol Hydrochloride; Bethanidine Sulfate; Bevantolol Hydrochloride; Biclodil Hydrochloride; Bisoprolol; Bisoprolol Fumarate; Bucindolol Hydrochloride; Bupicomide; Buthiazide: Candoxatril; Candoxatrilat; Captopril; Carvedilol; Ceronapril; Chlorothiazide Sodium; Cicletanine; Cilazapril; Clonidine; Clonidine Hydrochloride; Clopamide; Cyclopenthiazide; Cyclothiazide; Darodipine; Debrisoquin Sulfate; Delapril Hydrochloride; Diapamide; Diazoxide; Dilevalol Hydrochloride; Diltiazem Malate; Ditekiren; Doxazosin Mesylate; Ecadotril; Enalapril Maleate; Enalaprilat; Enalkiren; Endralazine Mesylate; Epithiazide; Eprosartan; Eprosartan Mesylate; Fenoldopam Mesylate; Flavodilol Maleate; Flordipine; Flosequinan; Fosinopril Sodium; Fosinoprilat; Guanabenz; Guanabenz Acetate; Guanacline Sulfate; Guanadrel Sulfate; Guancydine; Guanethidine Monosulfate; Guanethidine Sulfate; Guanfacine Hydrochloride; Guanisoquin Sulfate; Guanoclor Sulfate; Guanoctine Hydrochloride; Guanoxabenz; Guanoxan Sulfate; Guanoxyfen Sulfate; Hydralazine Hydrochloride; Hydralazine Polistirex; Hydroflumethiazide; Indacrinone; Indapamide; Indolaprif Hydrochloride; Indoramin; Indoramin Hydrochloride; Indorenate Hydrochloride; Lacidipine; Leniquinsin; Levcromakalim; Lisinopril; Lofexidine Hydrochloride; Losartan Potassium; Losulazine Hydrochloride; Mebutamate; Mecamylamine Hydrochloride; Medroxalol; Medroxalol Hydrochloride; Methalthiazide; Methyclothiazide; Methyldopa; Methyldopate Hydrochloride; Metipranolol; Metolazone; Metoprolol Fumarate; Metoprolol Succinate; Metyrosine; Minoxidil ; Monatepil Maleate; Muzolimine; Nebivolol; Nitrendipine; Ofornine; Pargyline Hydrochloride; Pazoxide; Pelanserin Hydrochloride; Perindopril Erbumine; Phenoxybenzamine Hydrochloride; Pinacidil; Pivopril; Polythiazide; Prazosin Hydrochloride; Primidolol; Prizidilol Hydrochloride; Quinapril Hydrochloride; Quinaprilat; Quinazosin Hydrochloride; Quinelorane Hydrochloride; Quinpirole Hydrochloride; Quinuclium Bromide; Ramipril; Rauwolfia Serpentina; Reserpine; Saprisartan Potassium; Saralasin Acetate; Sodium Nitroprusside; Sulfinalol Hydrochloride; Tasosartan; Teludipine Hydrochloride; Temocapril Hydrochloride; Terazosin Hydrochloride; Terlakiren; Tiamenidine; Tiamenidine Hydrochloride; Ticrynafen; Tinabinol; Tiodazosin; Tipentosin Hydrochloride; Trichlormethiazide; Trimazosin Hydrochloride; Trimethaphan Camsylate; Trimoxamine Hydrochloride; Tripamide; Xipamide; Zankiren Hydrochloride; Zofenoprilat Arginine.

Anti-inflammatory: Alclofenac; Alclometasone Dipropionate; Algestone Acetonide; Alpha Amylase; Amcinafal; Amcinafide; Amfenac Sodium; Amiprilose Hydrochloride; Anakinra; Anirolac; Anitrazafen; Apazone; Balsalazide Disodium; Bendazac; Benoxaprofen; Benzydamine Hydrochloride; Bromelains; Broperamole; Budesonide; Carprofen; Cicloprofen; Cintazone; Cliprofen; Clobetasol Propionate; Clobetasone Butyrate; Clopirac; Cloticasone Propionate; Cormethasone Acetate; Cortodoxone; Deflazacort; Desonide; Desoximetasone; Dexamethasone Dipropionate; Diclofenac Potassium; Diclofenac Sodium; Diflorasone Diacetate; Diflumidone Sodium; Diflunisal; Difluprednate; Diftalone; Dimethyl Sulfoxide; Drocinonide; Endrysone; Enlimomab; Enolicam Sodium; Epirizole; Etodolac; Etofenamate; Felbinac; Fenamole; Fenbufen; Fenclofenac; Fenclorac; Fendosal; Fenpipalone; Fentiazac; Flazalone; Fluazacort; Flufenamic Acid; Flumizole; Flunisolide Acetate; Flunixin; Flunixin Meglumine; Fluocortin Butyl; Fluorometholone Acetate; Fluquazone; Flurbiprofen; Fluretofen; Fluticasone Propionate; Furaprofen; Furobufen; Halcinonide; Halobetasol Propionate; Halopredone Acetate; Ibufenac; Ibuprofen; Ibuprofen Aluminum; Ibuprofen Piconol; Ilonidap; Indomethacin; Indomethacin Sodium; Indoprofen; Indoxole; Intrazole; Isoflupredone Acetate; Isoxepac; Isoxicam; Ketoprofen; Lofemizole Hydrochloride; Lornoxicam; Loteprednol Etabonate; Meclofenamate Sodium; Meclofenamic Acid; Meclorisone Dibutyrate; Mefenamic Acid; Mesalamine; Meseclazone; Methylprednisolone Suleptanate; Momiflumate; Nabumetone; Naproxen; Naproxen Sodium; Naproxol; Nimazone; Olsalazine Sodium; Orgotein; Orpanoxin; Oxaprozin; Oxyphenbutazone; Paranyline Hydrochloride; Pentosan Polysulfate Sodium; Phenbutazone Sodium Glycerate; Pirfenidone; Piroxicam; Piroxicam Cinnamate; Piroxicam Olamine; Pirprofen; Prednazate; Prifelone; Prodolic Acid; Proquazone; Proxazole; Proxazole Citrate; Rimexolone; Romazarit; Salcolex; Salnacedin; Salsalate; Sanguinarium Chloride; Seclazone; Sermetacin; Sudoxicam; Sulindac; Suprofen; Talmetacin; Talniflumate; Talosalate; Tebufelone; Tenidap; Tenidap Sodium; Tenoxicam; Tesicam; Tesimide; Tetrydamine; Tiopinac; Tixocortol Pivalate; Tolmetin; Tolmetin Sodium; Triclonide; Triflumidate; Zidometacin; Zomepirac Sodium.

Antinauseant: Buclizine Hydrochloride; Cyclizine Lactate; Naboctate Hydrochloride.

Antineutropenic: Filgrastim; Lenograstim; Molgramostim; Regramostim; Sargramostim.

Antiobsessional agent: Fluvoxamine Maleate.

Antiparkinsonian: Benztropine Mesylate; Biperiden; Biperiden Hydrochloride; Biperiden Lactate; Carmantadine; Ciladopa Hydrochloride; Dopamantine; Ethopropazine Hydrochloride; Lazabemide; Levodopa; Lometraline Hydrochloride; Mofegiline Hydrochloride; Naxagolide Hydrochloride; Pareptide Sulfate; Procyclidine Hydrochloride; Quinetorane Hydrochloride; Ropinirole Hydrochloride; Selegiline Hydrochloride; Tolcapone; Trihexyphenidyl Hydrochloride. Antiperistaltic: Difenoximide Hydrochloride; Difenoxin; Diphenoxylate Hydrochloride; Fluperamide; Lidamidine Hydrochloride; Loperamide Hydrochloride; Malethamer; Nufenoxole; Paregoric.

Antipsychotic: Acetophenazine Maleate; Alentemol Hydrobromide; Alpertine; Azaperone; Batelapine Maleate; Benperidol; Benzindopyrine Hydrochloride; Brofbxine; Bromperidol; Bromperidol Decanoate; Butaclamol Hydrochloride; Butaperazine; Butaperazine Maleate; Carphenazine Maleate; Carvotroline Hydrochloride; Chlorpromazine; Chlorpromazine Hydrochloride; Chlorprothixene; Cinperene; Cintriamide; Clomacran Phosphate; Clopenthixol; Clopimozide; Clopipazan Mesylate; Cloroperone Hydrochloride; Clothiapine; Clothixamide Maleate; Clozapine; Cyclophenazine Hydrochloride; Droperidol; Etazolate Hydrochloride; Fenimide; Flucindole; Flumezapine;

Fluphenazine Decanoate; Fluphenazine Enanthate; Fluphenazine Hydrochloride; Fluspiperone; Fluspirilene; Flutroline; Gevotroline Hydrochloride; Halopemide; Haloperidol; Haloperidol Decanoate; Iloperidone; Imidoline Hydrochloride; Lenperone; Mazapertine Succinate; Mesoridazine; Mesoridazine Besylate; Metiapine; Milenperone; Milipertine; Molindone Hydrochloride; Naranol Hydrochloride; Neflumozide Hydrochloride; Ocaperidone; Olanzapine; Oxiperomide; Penfluridol; Pentiapine Maleate; Perphenazine; Pimozide; Pinoxepin Hydrochloride; Pipamperone; Piperacetazine; Pipotiazine Palniitate; Piquindone Hydrochloride; Prochlorperazine Edisylate; Prochlorperazine Maleate; Promazine Hydrochloride; Remoxipride; Remoxipride Hydrochloride; Rimcazole Hydrochloride; Seperidol Hydrochloride; Sertindole; Setoperone; Spiperone; Thioridazine; Thioridazine Hydrochloride; Thiothixene; Thiothixene Hydrochloride; Tioperidone Hydrochloride; Tiospirone Hydrochloride; Trifluoperazine Hydrochloride; Trifluperidol; Triflupromazine; Triflupromazine Hydrochloride; Ziprasidone Hydrochloride.

Appetite suppressant: Dexfenfluramine Hydrochloride; Phendimetrazine Tartrate; Phentermine Hydrochloride.

Blood glucose regulators: Human insulin; Glucagon; Tolazamide; Tolbutamide; Chloropropamide; Acetohexamide and Glipizide.

Carbonic anhydrase inhibitor: Acetazolamide; Acetazolamide Sodium, Dichlorphenamide; Dorzolamide Hydrochloride; Methazolamide; Sezolarmide Hydrochloride.

Cardiac depressant: Acecainide Hydrochloride; Acetylcholine Chloride; Actisomide; Adenosine; Amiodarone; Aprindine; Aprindine Hydrochloride; Artilide Fumarate; Azimilide Dihydrochloride; Bidisomide; Bucainide Maleate; Bucromarone; Butoprozine Hydrochloride; Capobenate Sodium; Capobenic Acid; Cifenline; Cifenline Succinate; Clofilium Phosphate; Disobutamide; Disopyramide; Disopyramide Phosphate; Dofetilide; Drobuline; Edifolone Acetate; Emilium Tosylate; Encainide Hydrochloride; Flecainide Acetate; Ibutilide Fumarate; Indecainide Hydrochloride; Ipazilide Fumarate; Lorajmine Hydrochloride; Lorcainide Hydrochloride; Meobentine Sulfate; Mexiletine Hydrochloride; Modecainide; Moricizine; Oxiramide; Pirmenol Hydrochloride; Pirolazamide; Pranolium Chloride; Procainamide Hydrochloride; Propafenone Hydrochloride; Pyrinoline; Quindonium Bromide; Quinidine Gluconate; Quinidine Sulfate; Recainam Hydrochloride; Recainam Tosylate; Risotilide Hydrochloride; Ropitoin Hydrochloride; Sematilide Hydrochloride; Suricainide Maleate; Tocainide; Tocainide Hydrochloride; Transcainide.

Cardiotonic: Actodigin; Amrinone; Bemoradan; Butopamine; Carbazeran; Carsatrin Succinate; Deslanoside; Digitalis; Digitoxin; Digoxin; Dobutamine; Dobutamine Hydrochloride; Dobutamine Lactobionate; Dobutamine Tartrate; Enoximone; Imazodan Hydrochloride; Indolidan; Isomazole Hydrochloride; Levdobutamine Lactobionate; Lixazinone Sulfate; Medorinone; Milrinone; Pelrinone Hydrochloride; Pimobendan; Piroximone; Prinoxodan; Proscillaridin; Quazinone; Tazolol Hydrochloride; Vesnarinone.

Cardiovascular agent: Dopexamine; Dopexamine Hydrochloride.

Choleretic: Dehydrocholic Acid; Fencibutirol; Hymecromone; Piprozolin; Sincalide; Tocamphyl.

Cholinergic: Aceclidine; Bethanechol Chloride; Carbachol; Demecarium Bromide; Dexpanthenol; Echothiophate Iodide; Isoflurophate; Methacholine Chloride; Neostigmine Bromide; Neostigmine Methylsulfate; Physostigmine; Physostigmine Salicylate; Physostigmine Sulfate; Pilocarpine; Pilocarpine Hydrochloride; Pilocarpine Nitrate; Pyridostigmine Bromide.

Cholinergic agonist: Xanomeline; Xanomeline Tartrate.

Cholinesterase Deactivator: Obidoxime Chloride; Pralidoxime Chloride; Pralidoxime Iodide; Pralidoxime Mesylate.

Coccidiostat: Arprinocid; Narasin; Semduramicin; Semduramicin Sodium.

Cognition adjuvant: Ergoloid Mesylates; Piracetam; Pramiracetam Hydrochloride; Pramiracetam Sulfate; Tacrine Hydrochloride.

Cognition enhancer: Besipirdine Hydrochloride; Linopirdine; Sibopirdine.

Hormone: Diethylstilbestrol; Progesterone; 17 hydroxy progesterone; Medroxyprogesterone; Norgestrel; Norethynodrel; Estradiol; Megestrol (Megace); Norethindrone; Levonorgestrel; Ethyndiol; Ethinyl estradiol; Mestranol; Estrone; Equilin; 17 alpha dihydroequilin; equilenin; 17 alpha dihydroequilenin; 17 alpha estradiol; 17 beta estradiol; Leuprolide (lupron); Glucagon; Testolactone; Clomiphene; Han memopausal gonadotropins; Human chorionic gonadotropin; Urofollitropin; Bromocriptine; Gonadorelin; Luteinizing hormone releasing hormone and analogs; Gonadotropins; Danazol; Testosterone; Dehydroepiandrosterone; Androstenedione; Dihydroestosterone; Relaxin; Oxytocin; Vasopressin; Folliculostatin; Follicle regulatory protein; Gonadoctrinins; Oocyte maturation inhibitor; Insulin growth factor; Follicle Stimulating Hormone; Luteinizing hormone; Tamoxifen.; Corticorelin Ovine Triftutate; Cosyntropin; Metogest; Pituitary, Posterior; Seractide Acetate; Somalapor; Somatrem; Somatropin; Somenopor; Somidobove.

Memory adjuvant: Dimoxamine Hydrochloride; Ribaminol.

Mental performance enhancer: Aniracetam.

Mood regulator: Fengabine.

Neuroleptic: Duoperone Fumarate; Risperidone.

Neuroprotective: Dizocilpine Maleate.

Psychotropic: Minaprine.

Relaxant: Adiphenine Hydrochloride; Alcuronium Chloride; Aminophylline; Azumolene Sodium; Baclofen; Benzoctamine Hydrochloride; Carisoprodol; Chlorphenesin Carbamate; Chlorzoxazone; Cinflumide; Cinnamedrine; Clodanolene; Cyclobenzaprine Hydrochloride; Dantrolene; Dantrolene Sodium; Fenalanide; Fenyripol Hydrochloride; Fetoxylate Hydrochloride; Flavoxate Hydrochloride; Fletazepam; Flumetramide;-Flurazepam Hydrochloride; Hexafluorenium Bromide; Isomylamine Hydrochloride; Lorbamate; Mebeverine Hydrochloride; Mesuprine Hydrochloride; Metaxalone; Methocarbamol; Methixene Hydrochloride; Nafomine Malate; Nelezaprine Maleate; Papaverine Hydrochloride; Pipoxolan Hydrochloride; Quinctolate; Ritodrine; Ritodrine Hydrochloride; Rolodine; Theophylline Sodium Glycinate; Thiphenamil Hydrochloride; Xilobam.

Sedative-hypnotic: Allobarbital; Alonimid; Alprazolam; Amobarbital Sodium; Bentazepam; Brotizolam; Butabarbital; Butabarbital Sodium; Butalbital; Capuride; Carboclo-ral; Chloral Betaine; Chloral Hydrate; Chlordiazepoxide Hydrochloride; Cloperidone Hydrochloride; Clorethate; Cyprazepam; Dexclamol Hydrochloride; Diazepam; Dichloralphenazone; Estazolam; Ethchlorvynol; Etomidate; Fenobam; Flunitrazepam; Fosazepam; Glutethimide; Halazepam; Lormetazepam; Mecloqualone; Meprobamate; Methaqualone; Midaflur; Paraldehyde; Pentobarbital; Pentobarbital Sodium; Perlapine; Prazepam; Quazepam; Reclazepam; Roletamide; Secobarbital; Secobarbital Sodium; Suproclone; Thalidomide; Tracazolate; Trepipam Maleate; Triazolam; Tricetamide; Triclofos Sodium; Trimetozine; Uldazepam; Zaleplon; Zolazepam Hydrochloride; Zolpidem Tartrate.

Serotonin antagonist: Altanserin Tartrate; Amesergide; Ketanserin; Ritanserin.

Serotonin inhibitor: Cinanserin Hydrochloride; Fenclonine; Fonazine Mesylate; Xylamidine Tosylate.

Serotonin receptor antagonist: Tropanserin Hydrochloride.

Stimulant: Amfonelic Acid; Amphetamine Sulfate; Ampyzine Sulfate; Arbutamine Hydrochloride; Azabon; Caffeine; Ceruletide; Ceruletide Diethylamine; Cisapride; Dazopride Fumarate; Dextroamphetamine; Dextroamphetamine Sulfate; Difluanine Hydrochloride; Dimefline Hydrochloride; Doxapram Hydrochloride; Etryptamine Acetate; Ethamivan; Fenethylline Hydrochloride; Flubanilate Hydrochloride; Flurothyl; Histamine Phosphate; Indriline Hydrochloride; Mefexamide; Methamphetamine Hydrochlo ride; Methylphenidate Hydrochloride; Pemoline; Pyrovalerone Hydrochloride; Xamoterol; Xamoterol Fumarate. Synergist: Proadifen Hydrochloride.

Thyroid hormone: Levothyroxine Sodium; Liothyronine Sodium; Liotrix.

Thyroid inhibitor: Methimazole; Propyithiouracil.

Thyromimetic: Thyromedan Hydrochloride.

Cerebral ischemia agents: Dextrorphan Hydrochloride.

Vasoconstrictor: Angiotensin Amide; Felypressin; Methysergide; Methysergide Maleate.

Vasodilator: Alprostadil; Azaclorzine Hydrochloride; Bamethan Sulfate; Bepridil Hydrochloride; Buterizine; Cetiedil Citrate; Chromonar Hydrochloride; Clonitrate; Diltiazem Hydrochloride; Dipyridamole; Droprenilamine; Erythrityl Tetranitrate; Felodipine; Flunarizine Hydrochloride; Fostedil; Hexobendine; Inositol Niacinate; Iproxamine Hydrochloride; Isosorbide Dinitrate; Isosorbide Mononitrate; Isoxsuprine Hydrochloride; Lidoflazine; Mefenidil; Mefenidil Fumarate; Mibefradil Dihydrochloride; Mioflazine Hydrochloride; Mixidine; Nafronyl Oxalate; Nicardipine Hydrochloride; Nicergoline; Nicorandil; Nicotinyl Alcohol; Nifedipine; Nimodipine; Nisoldipine; Oxfenicine; Oxprenolol Hydrochloride; Pentaerythritol Tetranitrate; Pentoxifylline; Pentrinitrol; Perhexiline Maleate; Pindolol; Pirsidomine; Prenylamine; Propatyl Nitrate; Suloctidil; Terodiline Hydrochloride; Tipropidil Hydrochloride; Tolazoline Hydrochloride; Xanthinol Niacinate.

Specifically, topiramate may be administered in combination with other medications to treat certain symptoms and disorders including:

I. Treatment of Binge Eating (Binge Eating Disorder, Bulimia Nervosa, Anorexia Nervosa with Binge eating) with serotonin re-uptake inhibitors (e.g., citalopram (CELEXA), clomipramine (ANAFRANIL)), fluoxetine (PROZAC), fluvoxamine (LUVOX), venlafaxine (EFFEXOR), other antidepressants (e.g., bupropion (WELLBUTRIN) nefazodone (SERZONE), tricyclics (e.g., NORPRAMIN and PAMELOR), trazodone (DESYREL), Substance P antagonists), psychostimulants, (e.g., d-amphetamine, phentermine; and sibutramine (MERIDIA)) and orlistat.

II. Treatment of overweight/obesity condition with sibutramine (MERIDIA); psychostimulants, (e.g., d-amphetamine, phentermine) and orlistat.

III. Treatment of nicotine addiction/smoking cessation with bupropion (ZYBAN), serotonin reuptake inhibitors, nicotine patches and gun, and other antidepressants.

IV. Treatment of alcohol abuse/dependence (alcoholism) with naltrexone (REVIA), serotonin reuptake inhibitors, and other antidepressants.

V. Treatment of other impulse control disorders (behavioral addictions) with serotonin reuptake inhibitors, lithium, valproic acid or divalproex sodium (e.g., DEPAKENE or DEPAKOTE), other antidepressants, naltrexone, atypical antipsychotics, (e.g., olanzapine (ZYPREXA), quetiapine (SEROQUEL), risperidone (RISPERDAL), ziprasidone) and other mood stabilizers (e.g., carbamazepine)

VI. Treatment of paraphilias/sexual addictions with serotonin reuptake inhibitors, lithium, divalproex sodium/ valproic acid, antiandrogen medications (e.g., medroxyprogesterone, gonadotropin-releasing hormone (GnRH) agonists), other antidepressants, and other mood stabilizers (e.g., carbamazepine).

When administered, the formulations of the invention are applied in pharmaceutically acceptable amounts and in pharmaceutically acceptable compositions. Such preparations may routinely contain salts, buffering agents, preservatives, compatible carriers, and optionally other therapeutic ingredients. When used in medicine the salts should be pharmaceutically acceptable, but non-pharmaceutically acceptable salts may conveniently be used to prepare pharmaceutically acceptable salts thereof and are not excluded from the scope of the invention. Such pharmacologically and pharmaceutically acceptable salts include, but are not limited to, those prepared from the following acids: hydrochloric, hydrobromic, sulfuric, nitric, phosphoric, maleic, acetic, salicylic, p-toluene sulfonic, tartaric, citric, methane sulfonic, formic, malonic, succinic, naphthalene-2-sulfonic, and benzene sulfonic. Also, pharmaceutically acceptable salts can be prepared as alkaline metal or alkaline earth salts, such as sodium, potassium or calcium salts.

Suitable buffering agents include: acetic acid and a salt (1–2% W/V); citric acid and a salt (1–3% W/V); boric acid and a salt (0.5–2.5% W/V); and phosphoric acid and a salt (0.8–2% W/V). Suitable preservatives include benzalkonium chloride (0.003–0.03% W/V); chlorobutanol (0.3–0.9% W/V); parabens (0.01–0.25% W/V) and thimerosal (0.004–0.02% W/V).

In the present invention, the sulfamide derivatives are administered in safe and effective amounts. An effective amount means that amount necessary to delay the onset of, inhibit the progression of, halt altogether the onset or progression of or diagnose the particular condition being treated. In general, an effective amount for treating an ICD will be that amount necessary to inhibit mammalian symptoms of the particular ICD in-situ. When administered to a subject, effective amounts will depend, of course, on the particular condition being treated; the severity of the condition; individual patient parameters including age, physical condition, size and weight; concurrent treatment; frequency of treatment; and the mode of administration. These factors are well known to those of ordinary skill in the art and can be addressed with no more than routine experimentation. It is preferred generally that a minimum dose be used, that is, the lowest safe dosage that provides appropriate relief of symptoms.

Dosage may be adjusted appropriately to achieve desired drug levels, locally or systemically. Generally, daily oral doses of active compounds will be from about 0.01 mg/kg per day to 2000 mg/kg per day. It is expected that IV doses in the range of about 1 to 1000 mg/cm$^3$ per day will be effective. In the event that the response in a subject is insufficient at such doses, even higher doses (or effective higher doses by a different, more localized delivery route) may be employed to the extent that patient tolerance permits. Continuous IV dosing over, for example 24 hours or multiple doses per day is contemplated to achieve appropriate systemic levels of compounds.

A variety of administration routes are available. The particular mode selected will depend of course, upon the particular drug selected, the severity of the disease state(s) being treated and the dosage required for therapeutic efficacy. The methods of this invention, generally speaking, may be practiced using any mode of administration that is medically acceptable, meaning any mode that produces effective levels of the active compounds without causing clinically unacceptable adverse effects. Such modes of administration include oral, rectal, sublingual, topical, nasal, transdermal or parenteral routes. The term "parenteral" includes subcutaneous, intravenous, intramuscular, or infusion. Intravenous routes are preferred.

The compositions may conveniently be presented in unit dosage form and may be prepared by any of the methods well known in the art of pharmacy. In general, the compositions are prepared by uniformly and intimately bringing the compounds into association with a liquid carrier, a finely divided solid carrier, or both, and then, if necessary, shaping the product.

Compositions suitable for oral administration may be presented as discrete units such as capsules, cachets, tablets, or lozenges, each containing a predetermined amount of the active compound. Other compositions include suspensions in aqueous liquors or non-aqueous liquids such as a syrup, an elixir, or an emulsion.

Other delivery systems can include time-release, delayed release or sustained release delivery systems. Such systems can avoid repeated administrations of the active compounds of the invention, increasing convenience to the subject and the physician. Many types of release delivery systems are available and known to those of ordinary skill in the art. They include polymer based systems such as polylactic and polyglycolic acid, polyanhydrides and polycaprolactone; nonpolymer systems that are lipids including sterols such as cholesterol, cholesterol esters and fatty acids or neutral fats such as mono-, di and triglycerides; hydrogel release systems; silastic systems; peptide based systems; wax coatings, compressed tablets using conventional binders and excipients, partially fused implants and the like. In addition, a pump-based hardware delivery system can be used, some of which are adapted for implantation.

A long-term sustained release implant also may be used. "Long-term" release, as used herein, means that the implant is constructed and arranged to deliver therapeutic levels of the active ingredient for at least 30 days, and preferably 60 days. Long-term sustained release implants are well known to those of ordinary skill in the art and include some of the release systems described above.

EXAMPLES

In the examples, patients were treated with open-label topiramate starting at 25 mg/qHS and the dosage increased by the patient in 25 mg increments as tolerated by the subjects until a response is seen up to a maximum of 1200 mg.

TABLE 1

Patients with Binge Eating Disorder (BED) Treated Clinically with Open-Label Topiramate (as of 12/16/98)

| Pt # | Pt ID | Reasons Topiramate Begun | Max Dose (mg/day) | Response |
|---|---|---|---|---|
| 1 | LJM | BD (BED) (Obesity) | 1200 | Remission of BD Remission of BED Loss of 107 lbs. |
| 2 | CEJ | BD BED Overweight | 150 | Mild improvement of BD, Moderate decrease of BED, Loss of 5 lbs. Discontinued due to sedation, cognitive dulling |
| 3 | JAC | BD BED Obesity | 1200 | Moderate improvement of BD. Remission of BED Loss of 50.5 lbs |
| 4 | JEB | BD BED Overweight | 900 | Moderate improvement of BD, Marked improvement of BED, Loss of 30.5 lbs. |
| 5 | KCW | BED Obesity Compulsive Buying (BD, in remission) | 100 100 | First trial: No response of BED, discontinued due to GI distress Second Trial: Worsening of BD Remission of BED Loss of 11 lbs. Remission of Compulsive Buying |
| 6 | JB | BED Overweight | 100 | No response of BED No weight change |

Key: BD = Bipolar Disorder; BED = Binge Eating Disorder; Pt. = patient; D/C = topiramate treatment discontinued; Cont.= topiramate treatment continued; GI = gastrointestinal

TABLE 2

Patients with Overeating, Overweight, and Obesity Treated Clinically with Topiramate (as of 12/16/98)

| Pt # | Pt ID | Reasons Topiramate Begun | Max dose (mg/day) | Response |
|---|---|---|---|---|
| 1 | BAA | BD Obesity (BED, in remission) | 700 | No response of BD Loss of 9 lbs. (293–284) |
| 2 | HTB | BD Overeating Overweight | 300 | Remission of BD Remission of overeating Loss of 16 lbs. (248–232) Discontinued 2° illness in remission |
| 3 | ADJ | BD Overeating, Overweight | 400 | Moderate improvement of BD Moderate improvement of overeating Loss of 7 lbs. (239–232) |
| 4 | TK | BD Overeating Overweight | 350 | No response of BD Mild improvement in overeating Loss of 5 lbs. (238–233) |
| 5 | JCJ | BD Overeating Overweight | 1. 250 2. 200 | First Trial: Worsening of BD Mild decrease of overeating Loss of 7 lbs. (152–145) Second Trial Mild improvement of BD Mild decrease of overeating Gain of 1 lb. (154–155 lbs.) |
| 6 | KDC | Overeating Overweight (BD, in remission) | 800 | Worsening of BD Loss of 9 lbs. (208–199 lbs) |

TABLE 2-continued

Patients with Overeating, Overweight, and Obesity Treated Clinically with Topiramate (as of 12/16/98)

| Pt # | Pt ID | Reasons Topiramate Begun | Max dose (mg/day) | Response |
|---|---|---|---|---|
| 7 | NLR | BD Overweight | 300 | Worsening of BD Loss of 46 lbs. (196–150 lbs.) Discontinued due to anorexia |
| 8 | PR | BD Overeating Overweight | 700 | Moderate improvement of BD Marked improvement in overeating Loss of 19 lbs. (185–166) Discontinued due to G.I. Distress |

Key: Pt. = patient; BD = Bipolar Disorder; BED = Binge Eating Disorder; D/C = topiramate treatment discontinued; cont = topiramate treatment continued; GI = gastrointestinal

What is claimed is:

1. A method for treating an Impulse Control Disorder comprising administering to a mammal afflicted with such condition a therapeutically effective amount for treating such condition of a compound of the formula I:

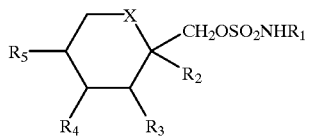

(I)

wherein

X is $CH_2$ or oxygen;

$R_1$ is hydrogen or alkyl; and $R_2$, $R_3$, $R_4$ and $R_5$ are independently hydrogen or lower alkyl and, when X is $CH_2$, $R_4$ and $R_5$ may be alkene groups joined to form a benzene ring and, when X is oxygen, $R_2$ and $R_3$ and/or $R_4$ and $R_5$ together may be a methylenedioxy group of the follow formula (II):

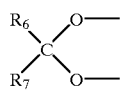

(II)

wherein $R_6$ and $R_7$ are the same or different and are hydrogen, lower alkyl or are alkyl and are joined to form a cyclopentyl or cyclohexyl ring;

wherein the Impulse Control Disorder is selected from the group consisting of intermittent explosive disorder (ED), kleptomania, pathological gambling, pyromania, trichotillomania, compulsive buying or shopping, repetitive self-mutilation, nonparaphilic sexual addictions, severe nail biting, compulsive skin picking, personality disorders with impulsive features, attention deficit/hyperactivity disorder, Binge Eating Disorder, bulimia nervosa, anorexia nervosa with binge eating and substance use disorders.

2. The method of claim 1 wherein the compound is selected from the group consisting of 2,3:4,5-bis-O-(1-methylethylidene)-beta-D-fructopyranose sulfamate;

2,3-O-(1-methylethylidene)-4,5-O-sulfonyl-beta-D-fructopyranose sulfamate;

2,3-O-(1-methylethylidene)-4,5-O-sulfonyl-beta-L-fructopyranose sulfamate;

2,3-O-(1-methylethylidene)-4,5-O-sulfonyl-beta-D-fructopyranose methylsulfamate;

2,3-O-(1-methylethylidene)-4,5-O-sulfonyl-beta-D-fructopyranose butylsulfamate;

2,3-O-(1-methylethylidene)-4,5-O-sulfonyl-beta-D-fructopyranose ethylsulfamate;

2,3-O-(1-methylethylidene)-4,5-O-sulfonyl-beta-D-fructopyranose octylsulfamate;

2,3-O-(1-methylethylidene)-4,5-O-sulfonyl-beta-D-fructopyranose 2-propenylsulfamate;

2,3-O-(1-methylethylidene)-4,5-O-sulfonyl-beta-D-fructopyranose phenylmethylsulfamate;

2,3-O-(1-methylethylidene)-4,5-O-sulfonyl-beta-D-fructopyranose cyclopropylsulfamate;

2,3-O-(1-methylethylidene)-4,5-O-sulfonyl-beta-D-fructopyranose cyclobutylsulfamate;

2,3-O-(1-methylethylidene)-4,5-O-sulfonyl-beta-D-fructopyranose (2,2,2-trifluoroethyl)sulfamate;

2,3-O-(1-methylethylidene)-4,5-O-sulfonyl-beta-D-fructopyranose dimethylsulfamate;

2,3-O-(1-methylethylidene)-4,5-O-sulfonyl-beta-D-fructopyranose diethylsulfamate;

2,3-O-(1-methylethylidene)-4,5-O-sulfonyl-beta-D-fructopyranose azido sulfamate;

(S)-2,3-O-(1-methylethylidene)-4,5-O-sulfinyl-beta-D-fructopyranose sulfamate;

(R)-2,3-O-(1-methylethylidene)-4,5-O-sulfinyl-beta-D-fructopyranose sulfamate;

2,3-O-(1-ethylpropylidene)-4,5-O-sulfonyl-beta-D-fructopyranose sulfamate;

2,3-O-(1-methylethylidene)-4,5-O-[N-(4-methylbenzenesulfonyl)imidosulfonyl]-beta-D-fructopyranose sulfamate;

2,3-O-(1-methylethylidene)-4,5-O-[N-(4-methylbenzenesulfonyl)imidosulfonyl]-beta-D-fructopyranose sulfamate;

2,3-O-(cyclohexylidene)-4,5-O-sulfonyl-beta-D-fructopyranose sulfamate;

(S)-4,5-O-[N-(1,1-dimethylethoxycarbonyl)imidosulfinyl]-2,3-O-(1-methylethylidene)-beta-D-fructopyranose sulfamate, and the pharmaceutically acceptable salts thereof.

3. The method of claim 1 wherein the compound is selected from the group consisting of (1R,2R,3S,4S)-(1,2:3,4-di-O-methylethylidenecyclohexan-1,2,3,4-tetrahydroxy-4-yl)methyl sulfamate and (1R,2S,3S,4S)-(3,4-O-methylethylidene-1,2-O-sulfinylcyclohexan-1,2,3,4-tetrahydroxy-4-yl)methyl sulfamate.

4. The method of claim 1 wherein the compound of formula I is topiramate.

5. The method of claim 1, wherein the therapeutically effective amount is of from about 15 to about 2000 mg per day.

6. The method of claim 1, wherein the therapeutically effective amount is of from about 25 to about 750 mg per day.

7. The method of claim 1 wherein the compound is used in conjunction with one or more other drug compounds selected from the group consisting of adrenergics, adrenocortical steroids, adrenocortical suppressants, aldosterone antagonists, amino acids, analeptics, analgesics, anorectic compounds, anorexics, anti-anxiety agents, antidepressants, antihypertensives, anti-inflammatorys, antinauseants, antineutropenics, antiobsessional agents, antiparkinsonians, antipsychotics, appetite suppressants, blood glucose regulators, carbonic anhydrase inhibitors, cardiotonics, cardiovascular agents, choleretics, cholinergics, cholinergic agonists, cholinesterase deactivators, cognition adjuvants, cognition enhancers, hormones, memory adjuvants, mental performance enhancers, mood regulators, neuroleptics, neuroprotectives, psychotropics, relaxants, sedative-hypnotics, serotonin antagonists, serotonin inhibitors, serotonin receptor antagonists, stimulants, thyroid hormones, thyroid inhibitors, thyromimetics, cerebral ischemia agents, vasoconstrictors, and vasodilators.

8. The method of claim 1 wherein the Impulse Control Disorder is an eating disorder and the compound is used in conjunction with one or more other drug compounds selected from the group consisting of serotonin re-uptake inhibitors, antidepressants, psychostimulants, and orlistat.

9. The method of claim 1 wherein the Impulse Control Disorder is a nicotine addiction condition and the compound is used in conjunction with one or more other drug compounds selected from the group consisting of bupropion, serotonin reuptake inhibitors, nicotine, and antidepressants.

10. The method of claim 1 wherein the Impulse Control Disorder is an alcohol abuse/dependence condition and the compound is used in conjunction with one or more other drug compounds selected from the group consisting of naltrexone, serotonin reuptake inhibitors, and other antidepressants.

11. The method of claim 1 wherein the Impulse Control Disorder is a behavioral addiction condition and the compound is used in conjunction with one or more other drug compounds selected from the group consisting of serotonin reuptake inhibitors, lithium, valproic acid or divalproex sodium, other antidepressants, naltrexone, atypical antipsychotics, and other mood stabilizers.

12. The method of claim 1 wherein the Impulse Control Disorder is a paraphilias/sexual addiction condition and the compound is used in conjunction with one or more other drug compounds selected from the group consisting of serotonin reuptake inhibitors, lithium, divalproex sodium/valproic acid, antiandrogen agents, other antidepressants, and other mood stabilizers.

13. A method for treating an Impulse Control Disorder comprising administering to a mammal afflicted with such condition a therapeutically effective amount for treating such condition of a compound of the formula I:

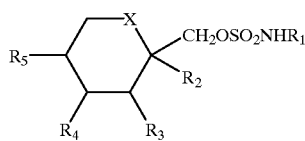

(I)

wherein

X is $CH_2$ or oxygen;

$R_1$ is hydrogen or alkyl; and $R_2$, $R_3$, $R_4$ and $R_5$ are independently hydrogen or lower alkyl and, when X is $CH_2$, $R_4$ and $R_5$ may be alkene groups joined to form a benzene ring and, when X is oxygen, $R_2$ and $R_3$ and/or $R_4$ and $R_5$ together may be a methylenedioxy group of the following formula (II):

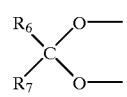

(II)

wherein $R_6$ and $R_7$ are the same or different and are hydrogen, lower alkyl or are alkyl and are joined to form a cyclopentyl or cyclohexyl ring;

wherein the Impulse Control Disorder is selected from the group consisting of intermittent explosive disorder (IED), kleptomania, pathological gambling, pyromania, trichotillomania, compulsive buying or shopping, repetitive self-mutilation, nonparaphilic sexual addictions, severe nail biting, compulsive skin picking, personality disorders with impulsive features, attention deficit/hyperactivity disorder, Binge Eating Disorder, anorexia nervosa with binge eating and substance use disorders.

14. A method for treating an Impulse Control Disorder comprising administering to a mammal afflicted with such condition a therapeutically effective amount for treating such condition of a compound of the formula I:

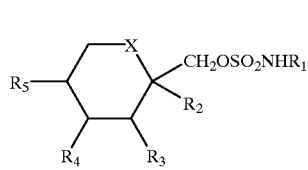

(I)

wherein

X is $CH_2$ or oxygen;

$R_1$ is hydrogen or alkyl; and $R_2$, $R_3$, $R_4$ and $R_5$ are independently hydrogen or lower alkyl and, when X is $CH_2$, $R_4$ and $R_5$ may be alkene groups joined to form a benzene ring and, when X is oxygen, $R_2$ and $R_3$ and/or $R_4$ and $R_5$ together may be a methylenedioxy group of the following formula (II):

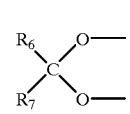

(II)

wherein $R_6$ and $R_7$ are the same or different and are hydrogen, lower alkyl or are alkyl and are joined to form a cyclopentyl or cyclohexyl ring; wherein the Impulse Control Disorder is bulimia nervosa.

15. A method for treating an Impulse Control Disorder characterized by binge eating, wherein the Impulse Control Disorder is selected from the group consisting of Binge Eating Disorder, Bulimia Nervosa and Anorexia Nervosa with Binge Eating, said method comprising administering to a human afflicted with such a disorder, a therapeutically effective amount of topiramate in combination with one or more drug compounds selected from the group consisting of serotonin re-uptake inhibitors, antidepressants, psychostimulants, orlistat, and sibutramine.

16. A method for treating an Impulse Control Disorder characterized by binge eating, wherein the Impulse Control Disorder is selected from the group consisting of Binge Eating Disorder, Bulimia Nervosa and Anorexia Nervosa with Binge Eating, said method comprising administering to a human afflicted with such a disorder, a therapeutically effective amount of topiramate in combination with a serotonin re-uptake inhibitor.

* * * * *